(12) United States Patent
Waluszko

(10) Patent No.: US 7,030,392 B2
(45) Date of Patent: Apr. 18, 2006

(54) ULTRAVIOLET LIGHTING PLATFORM

(76) Inventor: Alex Waluszko, 2066 W. 11th St., Upland, CA (US) 91786

( * ) Notice: Subject to any disclaimer, the term of this patent is extended or adjusted under 35 U.S.C. 154(b) by 239 days.

(21) Appl. No.: 10/733,561

(22) Filed: Dec. 10, 2003

(65) Prior Publication Data

US 2005/0127308 A1 Jun. 16, 2005

(51) Int. Cl.
*H05B 35/00* (2006.01)
(52) U.S. Cl. .............................. 250/455.11; 250/504 R; 250/505.1
(58) Field of Classification Search .......... 250/455.11, 250/504 R, 505.1; 362/230, 231
See application file for complete search history.

(56) References Cited

U.S. PATENT DOCUMENTS

| | | | |
|---|---|---|---|
| 3,936,186 A | 2/1976 | Boland et al. | |
| 4,095,113 A | 6/1978 | Wolff | |
| 4,287,554 A | 9/1981 | Wolff | |
| 4,309,616 A | 1/1982 | Wolff | |
| 4,591,958 A | 5/1986 | Lamboo | |
| 4,657,655 A | 4/1987 | Smoot et al. | |
| 4,872,741 A | 10/1989 | Dakin | |
| 5,175,437 A | 12/1992 | Waluszko | |
| 5,220,249 A | 6/1993 | Tsukada | |
| 5,248,917 A | 9/1993 | Hamagishi et al. | |
| 5,288,647 A | 2/1994 | Zimlich, Jr. et al. | |
| 5,327,195 A | 7/1994 | Ehr | |
| 5,347,342 A | 9/1994 | Ehr | |
| 5,387,801 A | 2/1995 | Gonzalez et al. | |
| 5,449,446 A | 9/1995 | Verma | |
| 5,502,626 A | 3/1996 | Armstrong et al. | |
| 5,631,734 A | 5/1997 | Stern et al. | |
| 5,645,663 A | 7/1997 | Nakayama | |
| 5,670,786 A | 9/1997 | Meyer et al. | |
| 5,717,284 A | 2/1998 | Anandan | |
| 5,717,602 A | 2/1998 | Kenning | |
| 5,731,658 A | 3/1998 | Lengyel et al. | |
| 5,736,744 A | 4/1998 | Johannsen | |
| 5,737,065 A | 4/1998 | Hansen | |
| 5,897,760 A | 4/1999 | Heffelfinger et al. | |
| 5,951,838 A | 9/1999 | Heffelfinger et al. | |
| 6,034,470 A | 3/2000 | Vollkommer | |
| 6,069,441 A | 5/2000 | Lengyel et al. | |
| 6,639,352 B1 | 10/2003 | Eom | |
| 6,670,619 B1 | 12/2003 | Waluszko | |
| 2005/0127303 A1* | 6/2005 | Waluszko | 250/374 |

FOREIGN PATENT DOCUMENTS

GB 1048606 6/1964

* cited by examiner

*Primary Examiner*—Kiet T. Nguyen
(74) *Attorney, Agent, or Firm*—James E. Brunton, Esq.

(57) ABSTRACT

A method and apparatus for genomic or proteomic research to visualize fluorescent labeled DNA, RNA or protein samples that have been separated for documentation and analysis. The apparatus includes a novel radiation source for uniformly irradiating the samples which comprises a grid constructed from a continuous, serpentine shaped ultraviolet light producing tube that is strategically formed to provide a multiplicity of side-by-side, immediately adjacent irradiating segments. In one form of the invention the apparatus also includes a first conversion plate that is carried by the housing at a location intermediate the radiation source and the sample supporting platform for converting the radiation emitted from the source to radiation at a second wavelength.

21 Claims, 7 Drawing Sheets

ULTRAVIOLET LIGHTING PLATFORM

BACKGROUND OF THE INVENTION

1. Field of the Invention

The present invention relates generally to ultraviolet radiation devices. More particularly, the invention concerns an apparatus for use in genomic or proteomic research to visualize fluorescent labeled DNA, RNA or protein samples that have been separated for documentation and analysis.

2. Discussion of the Prior Art

By way of brief background, ultraviolet light (UV), which is electromagnetic radiation in the region of the spectrum located between X-rays and visible light, is typically divided into three principal ranges, namely long wave, mid-range, and short wave. For each of these UV ranges specific applications have been developed.

As a general rule, the desired ultraviolet wavelength is obtained from a fluorescent style tube that is an electric discharge device that uses a low-pressure mercury vapor arc to generate ultraviolet energy. The ultraviolet energy released in typical, commercially available fluorescent tubes is primarily at the wavelength of about 254 nanometers. However, the fluorescent tubes can be modified to release other ultraviolet wavelengths by the use of phosphors, which have the ability to absorb the ultraviolet energy and re-radiate it in other wavelengths. For example, long wave ultraviolet of about 365 nanometers and mid-range ultraviolet of about 300 nanometers are created by coating the inside of the fluorescent tubes with the proper phosphors which convert the short wave ultraviolet.

In the past ultraviolet irradiation of selected articles has been accomplished using a single UV range fluorescent tube mounted within a suitable enclosure. In order to eliminate white light generated by the UV tube, some prior art devices make use of a UV transmitting ambient or visible light blocking filter that is typically mounted in front of the UV tube.

By way of example, U.S. Pat. No. 5,175,347 issued to the present inventor describes an apparatus for irradiating an object such as a specimen of material with ultraviolet radiation at a selected long, short or mid-wave length. Similarly, U.S. Pat. No. 3,936,186 issued to Boland et al discloses an apparatus for exposing diazo printing plates and the like of the character that are used in the graphic arts field. In like manner, U.S. Pat. No. 5,288,647 issued Zimlich, Jr. et al relates to a method by which polynucleotide specimens can be irradiated particularly for the purpose of fixing them to a substrate. Similarly, patent U.S. Pat. No. 5,736,744 issued to Johannsen et al., in which the present inventor is named as a coinventor, discloses a wave length shifting filter separate and apart from a transilluminator. The wavelength shifting filter uses phosphors in a flat array to provide a selection of visible wavelengths.

U.S. Pat. No. 5,951,838 issued to Heffelfinger et al., concerns a method and apparatus for achieving uniform illumination of an electrophoresis apparatus. In the Heffelfinger et al. method, uniform illumination is achieved by scanning the light source across the sample gel in a direction perpendicular to the axis of the source. The light source is comprised of one or more light bulbs placed in a light tray. Variations in light intensity near the source end portions is minimized using a variety of techniques including extended light bulbs, filters, reflectors, and diffusers, or supplemental sources.

The standard prior art method for separating, identifying and purifying biological samples is electrophoresis through a gel. The electrophoresis process is simple and well understood today. It is commonly used in one dimension separation where distinct bands of distinct biologicals are formed, or in two dimension separation where distinct spots or bands are formed.

Generally, following the process of electrophoretic separation, the separated biological samples are stained with a fluorescent dye, such as ethidium bromide. A set of multiple visible fluorescing dyes can be utilized that are capable of identifying specifically separated biological samples. These dyes have the ability to specifically attach (tag) themselves to specific biological samples and fluoresce in different visible wavelengths.

After the sample is dyed it is exposed to an ultraviolet radiation source, normally within the spectral bandwidth of mid-range ultraviolet (280 nm–320 nm). This range generally provides for the best and brightest wave shift conversion of the dye. During exposure, the dye labeled, separated biological sample is visible for viewing, documentation and further analysis. It is to be noted that other wavelengths of ultraviolet, such as short wave ultraviolet (generally considered as 254 nm), long wave ultraviolet (320–400 nm), broadband ultraviolet and a combination of short wave, mid-range and long wave can also be used to generate the fluorescent wave shift action of the dyes.

Although excitation of the fluorescent labeled biological sample is at times possible with visible wavelengths and light boxes that generate visible wavelengths, such as 420 nm or 480 nm, it is generally understood that UV excitation allows larger stoke shifts (that is the discrimination between excitation and emission wavelengths), enables higher signal to noise ratios and provides greater sensitivity.

A commonly used prior art tool for illuminating electrophoretically separated gels is the ultraviolet transilluminator (light box). These light boxes, generally comprise a single wavelength set of ultraviolet producing fluorescent lamps. These lamps are generally horizontally mounted within the light box behind a window upon which the dye labeled sample rests. The window typically comprises an ultraviolet transmitting, ambient (visible) light blocking filter material. Other ultraviolet light boxes are commercially available that provide dual UV wavelength combinations of 254 nm/365 nm, 254 nm/302 nm and 365 nm/302 nm. In this regard, commercially available mid-range ultraviolet light boxes interchangeably use the wavelength designations 300 nm, 302 nm, 310 nm or 312 nm, since the UV bandwidth output of these wavelength designations is substantially the same. Additionally, UV light boxes are commercially available that provide all three UV wavelengths of 254 nm, 302 nm and 365 nm. However, substantially all presently commercially available ultraviolet transilluminators (light boxes) use commercially available ultraviolet producing lamps that singly provide UV wavelengths in 365 (UV-A bandwidth), 302 nm (UV-B bandwidth) and 254 nm (UV-C bandwidth).

Another device used to capture fluorescent labeled biological samples is commercially available from Bio-Rad, Inc. of Hercules, Calif. under the name and style FLUOR S MULTIMAGER. This device uses a single broadband (290 nm–365 nm) ultraviolet fluorescent lamp. This ultraviolet fluorescent style tube lamp is horizontally mounted below the sample holding window and is typically scanned across the sample permitting the acquisition of the fluorescent signal via a charge coupled device (CCD) based camera system. This configuration limits the actual viewing of the fluorescent labeled sample by the researcher in real-time. The previously mentioned U.S. Pat. No. 5,951,838 issued to Heffelfinger, et al. and entitled "Method and Apparatus for Correcting Illumination Non-Uniformities" describes this method in greater detail.

As a general rule, all commercially available ultraviolet light boxes use 4, 5, or 6 fluorescent style UV generating lamps. These UV fluorescent lamps (254 nm, 302 nm, 365 nm or broadband) are typically commercially available in 4 watt, 6 watt, 8 watt, 15 watt and 25 watt styles and in varying lengths. The lamps are normally configured in a horizontal pattern and are generally superimposed over a reflective aluminum reflector. Typically, a UV transmitting—ambient visible light blocking filter is positioned above the lamps.

It is well understood that conventional ultraviolet generating fluorescent style tube lamps of the type described in the preceding paragraph generate ultraviolet radiation in an arc formed between the electrodes in the lamp. However it is not well known that the intensity or output of this type of lamp diminishes from the center point of the arc towards the arc origination points. Accordingly, in virtually all wattages and configurations, the presently commercially available lamps provide a sample illumination surface that is substantially non-uniform. This problem of non-uniform UV illumination of fluorescent biologically labeled samples has been addressed in the past by the development of data manipulation and correction software that is specially designed to account for UV background on a fluorescent labeled sample. A description of such software and of its use is discussed in detail in U.S. Pat. Nos. 5,951,838 and 5,897,760 issued to Heffelfinger, et al.

Other prior art devices suggest the use of a cold cathode type serpentine grid to generate a more uniform visible light for use in LCD and photographic film viewing background lighting. A description of such prior art devices can be found in U.S. Pat. Nos. 5,731,658 and 6,069,441 issued to Lengyel et al.

Commercially available alternatives to the ultraviolet light box are available in devices that use lasers to illuminate the fluorescent labeled biological samples. Typically, these devices rely on laser light sources to illuminate the fluorescent "tagged" samples to excite the samples. In such devices, the laser source is scanned serially to excite each sample.

As will be better understood from the discussion that follows, the present invention overcomes many of the drawbacks of the prior art devices.

SUMMARY OF THE INVENTION

The present invention provides a method and apparatus for use in genomic or proteomic research to visualize fluorescent labeled DNA, RNA or protein samples that have been separated for documentation and analysis. By way of summary, one form of the apparatus of the invention comprises a housing having interconnected top, bottom, and side walls defining an internal chamber and a sample supporting platform having a sample supporting area and radiation means disposed within the chamber for uniformly irradiating the sample supporting area with ultraviolet light at a first wavelength. The radiation means uniquely comprises a grid for emitting ultraviolet radiation constructed from a continuous, serpentine shaped ultraviolet tube that is strategically formed to provide a multiplicity of side-by-side, immediately adjacent irradiating segments. In one form of the invention the apparatus also includes a first conversion means that is removably carried by the housing at a location intermediate the radiation means and the sample supporting platform for converting the radiation emitted from said source of ultraviolet radiation to radiation at a second wavelength.

With the foregoing in mind, it is an object of the present invention to provide a method and apparatus in which the uniformity of excitation radiation across the sample supporting surface of the apparatus is vastly improved when compared with the nonuniformity of radiation across the sample supporting surface of prior art transilluminators. More particularly, it is an object of the invention to provide apparatus of the character described in which the Coefficient of Variation is well below about 5 to 10%.

Another object of the invention is to provide a method and apparatus of the character described in the preceding paragraphs in which meaningful, quantitative side by side comparisons of samples are possible.

Another object of the invention is to provide a method and apparatus in which sequential analysis of several samples is greatly simplified and is substantially more accurate than is possible with prior art transilluminators because of the minimal effect on excitation intensity of sample positioning on the sample support surface. More particularly, it is an object of the invention to provide a method and apparatus in which the same sample will give similar fluorescent intensities regardless of where the sample is placed on the sample supporting surface of the apparatus.

Another object of the invention is to provide a novel radiation source for uniformly irradiating a spaced apart surface with an ultraviolet radiation, the radiation source comprising a uniquely configured grid constructed from a continuous, serpentine shaped ultraviolet tube.

The foregoing as well as other objectives of the invention will become apparent from the description which follows.

DESCRIPTION OF THE INVENTION

Figure 1:
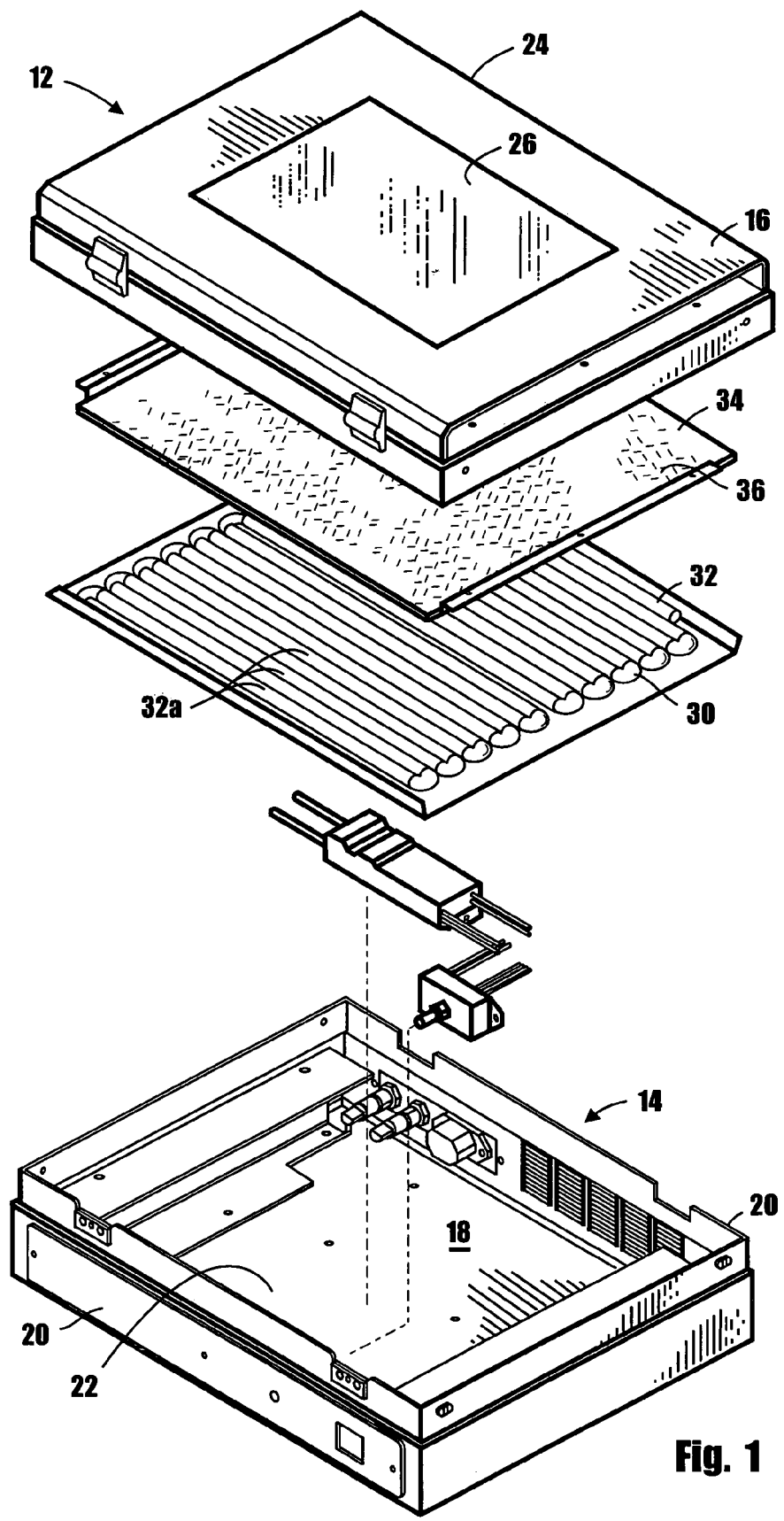
FIG. 1 is a generally perspective, exploded view of one form of the apparatus of the invention for uniformly illuminating molecular samples with ultraviolet radiation.

Referring to the drawings and particularly to FIG. 1, one form of the apparatus of the invention for uniformly illuminating molecular samples with ultraviolet radiation is there shown and generally designated by the numeral 12. The apparatus of this form of the invention comprises a housing 14 having interconnected top, bottom and sidewalls 16, 18, and 20 respectively that define an internal chamber 22. Carried by top wall 16 is a sample supporting platform 24 having a sample supporting area or surface 26.

An important aspect of the apparatus of the present invention comprises radiation means disposed within chamber 22 for uniformly irradiating the sample supporting area with ultraviolet light at a first wavelength. This novel radiation means here comprises a uniquely configured grid 30 for uniformly emitting ultraviolet radiation. Grid 30 is here constructed from a continuous, serpentine shaped ultraviolet producing tube 32 that is strategically formed to provide a multiplicity of side-by-side, immediately adjacent irradiating segments 32a. As will be discussed in greater detail hereinafter, grid 30 is custom-designed and constructed to uniquely provide in conjunction with the conversion and dispersion means of the invention, a uniform illumination of the sample supporting area which is of the character illustrated in FIG. 3 of the drawings.

Figure 2:
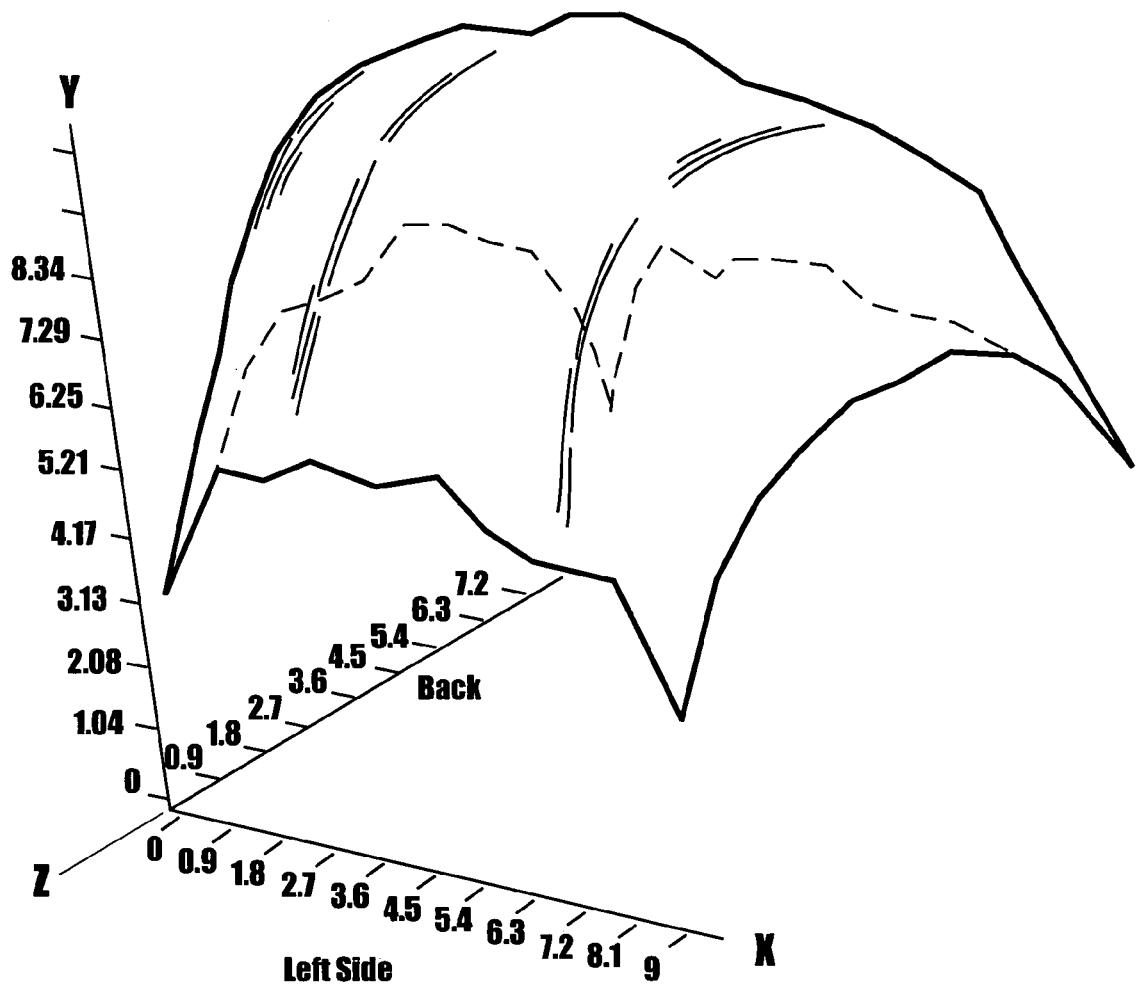
FIG. 2 is a generally perspective, diagrammatic view illustrating the non-uniform illumination of a sample supporting surface by a conventional, prior art transilluminator using a plurality of standard, side-by-side fluorescent type UV lamps.
Figure 3:
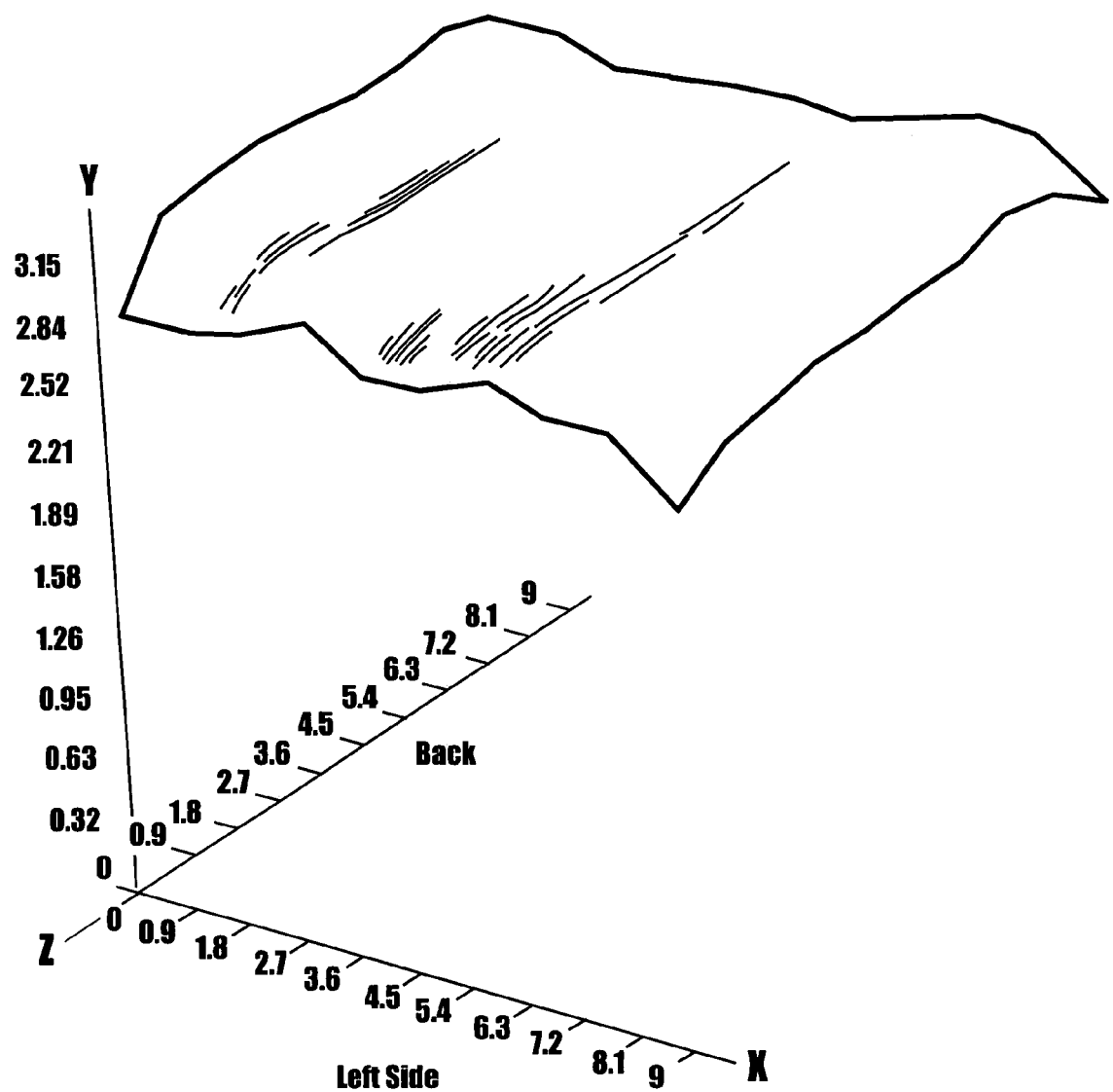
FIG. 3 is a generally perspective, diagrammatic view illustrating the uniform illumination of a sample supporting surface by the uniquely configured ultraviolet radiation emitting grid of the apparatus of the present invention.

By comparing the illumination pattern of a prior art transilluminator as illustrated in FIG. 2 of the drawings, with the illumination pattern of the apparatus of the present invention as illustrated in FIG. 3 of the drawings, it is at once apparent that the uniquely configured grid 30 of the apparatus of the present invention when combined with the conversion and dispersion means of the invention produces a vastly superior illumination of the sample supporting area than does the conventional transilluminator which embodies a plurality of standard, side-by-side fluorescent tubes.

An important aspect of the apparatus of the present invention is the previously mentioned, first conversion means that it is carried by housing 14 at a location intermediate the radiation means, or grid 30, and the superimposed supporting surface 26 platform 24. This important first conversion means functions to convert the radiation emitted from the source of ultraviolet radiation, or grid 30, at a first wavelength of, for example 254 nanometers, to radiation at a second wavelength. This first wavelength conversion means here comprises a conversion plate 34 that is carried within the internal chamber of housing 14 at a location intermediate the sample supporting platform and the UV source 30. More particularly, plate 34 is provided with a conventional wave shifting phosphor coating 36. As is well known in the art, phosphors are compounds that are capable of emitting useful quantities of radiation in the visible and/or ultraviolet spectrums upon excitation of the material by an external energy source. Due to this property, phosphor compounds have long been utilized in cathode ray tube (CRT) screens for televisions and similar devices. Typically, inorganic phosphor compounds include a host material doped with a small amount of an activator ion. In recent years, phosphor compounds, including phosphors in particular form, have been used in display devices, decorations, cathode ray tubes and fluorescent lighting fixtures. Luminescence or light emission by phosphor particles may be stimulated by application of heat (thermo luminescence), light (photo luminescence), high energy radiation (e.g., x-rays or e-beams), or electric fields (Electro luminescence).

A comprehensive discussion of various types of phosphors can be found in Pat. No. 6,193,908 issued to Hampden-Smith et al.

Figure 4:
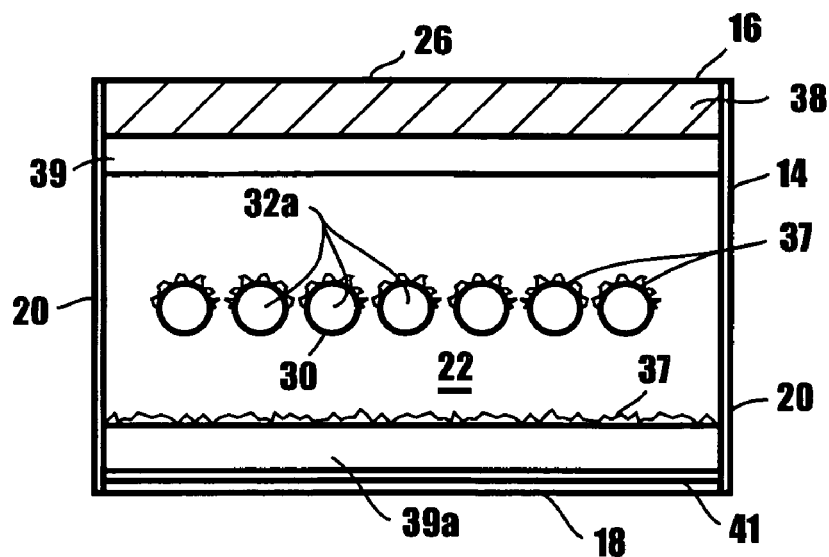
FIG. 4 is a generally diagrammatic, cross-sectional view of an alternate form of the apparatus of the invention.
Figure 5:
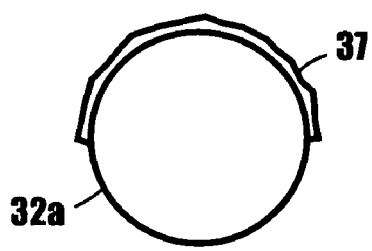
FIG. 5 is a greatly enlarged cross-sectional view of one of the grid segments of the radiation grid of the apparatus showing the segment coated with a phosphor coating.

Referring next to FIGS. 4 and 5, still another form of transilluminator of the invention is there shown in generally diagrammatic form. This embodiment of the invention is also similar in many respects to that shown in FIG. 1 and like numerals are used in FIGS. 4 and 5 to identify like components. This alternate form of the invention comprises a housing 14 having interconnected top, bottom and sidewalls 16, 18 and 20 respectively that define an internal chamber 22. As before, top wall 16 includes a sample supporting area 26.

Positioned between the radiation means or grid 30, are first and second wavelength conversion means which are adapted to convert the UV radiation at the first wavelength of for example, 254 nanometers and then to UV radiation at a second wavelength of, for example 302 nanometers. This first wavelength conversion means here comprises a phosphor coating 37 on the upper surface of each of the grid segments 32a. The second wavelength conversion means here comprises a UV transmitting white light blocking filter 38 that is carried by a first borosilicate plate 39 which is located intermediate the sample support area and the grid 30. As well as understood by those skilled in the art, borosilicate does not block visible light or infrared, but does minimize 254 nm UV.

Also forming a part of the apparatus of this latest form of the invention is a reflector 41, which is carried by the bottom wall of housing 14. Superimposed over reflector 41 is a second borosilicate plate 39a which is coated with a phosphor coating 37. With this construction grid 30 irradiates the phosphor coating on the second borosilicate plate 39b converting the 254 nanometer radiation to 302 nanometers. The 302 nanometer radiation radiates upwardly and downwardly, passes through the plate 39a and impinges upon reflector 41. Reflector 41 then reflects the radiation in an upwardly direction through plate 39 and upwardly of chamber 22. The reflected radiation is added to the radiation produced by the phosphor that coats the upper half of the segments of the grid, the upward radiation generated by means of plate 39a and all the combined radiation passes upwardly through filter 38 and impinges on the samples resting on the sample supporting or surface area 26.

Figure 4A:
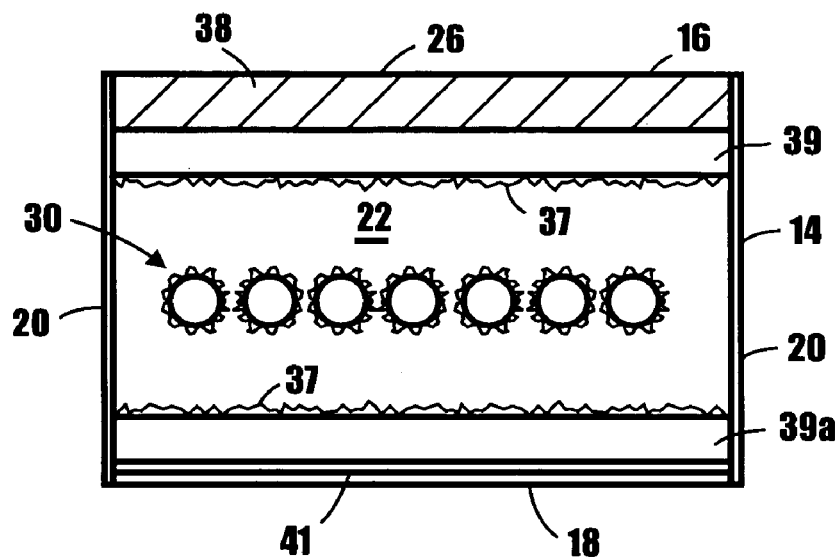
FIG. 4A is a generally diagrammatic, cross-sectional view of still another form of the apparatus of the invention.

Referring next to FIG. 4A, yet another form of transilluminator of the invention is there shown in generally diagrammatic form. This embodiment of the invention is also similar in many respects to that shown in FIG. 4 and like numerals are used in FIG. 4A to identify like components. This alternate form of the invention comprises a housing 14 having interconnected top, bottom and sidewalls 16, 18 and 20 respectively that define an internal chamber 22. As before, top wall 16 includes a sample supporting area 26.

Positioned between the radiation means, or grid 30, and the sample supporting area 26 is a wavelength conversion means which is adapted to convert the UV radiation at the first wavelength of, for example, 254 nanometers to UV radiation at a second wavelength of, for example, 302 nanometers. This first wavelength conversion means here comprises a phosphor coating 37 disposed on the lower surface of a borosilicate plate 39 that is located between the sample supporting area and the grid in the manner shown in FIG. 4A.

Also forming a part of the apparatus of this latest form of the invention is a reflector 41, which is carried by the bottom wall of housing 14. Superimposed over reflector 41 is a second borosilicate plate 39a which is coated with a phosphor coating 37. With this construction, downwardly directed radiation from grid 30 irradiates the phosphor coating on the second borosilicate plate 39b converting the 254 nanometer radiation to 302 nanometers. The 302 nanometer radiation then passes through the plate 39a and impinges on reflector 41. Reflector 41 then reflects the radiation upwardly where it impinges upon the phosphor coating 37 provided on the lower surface of plate 39. The radiation thus produced is added to the upwardly reflected radiation and the combined radiation from both plates 39 and 39a passes through filter 38 and impinges on the samples resting on the sample supporting or surface area 26.

Figure 6:
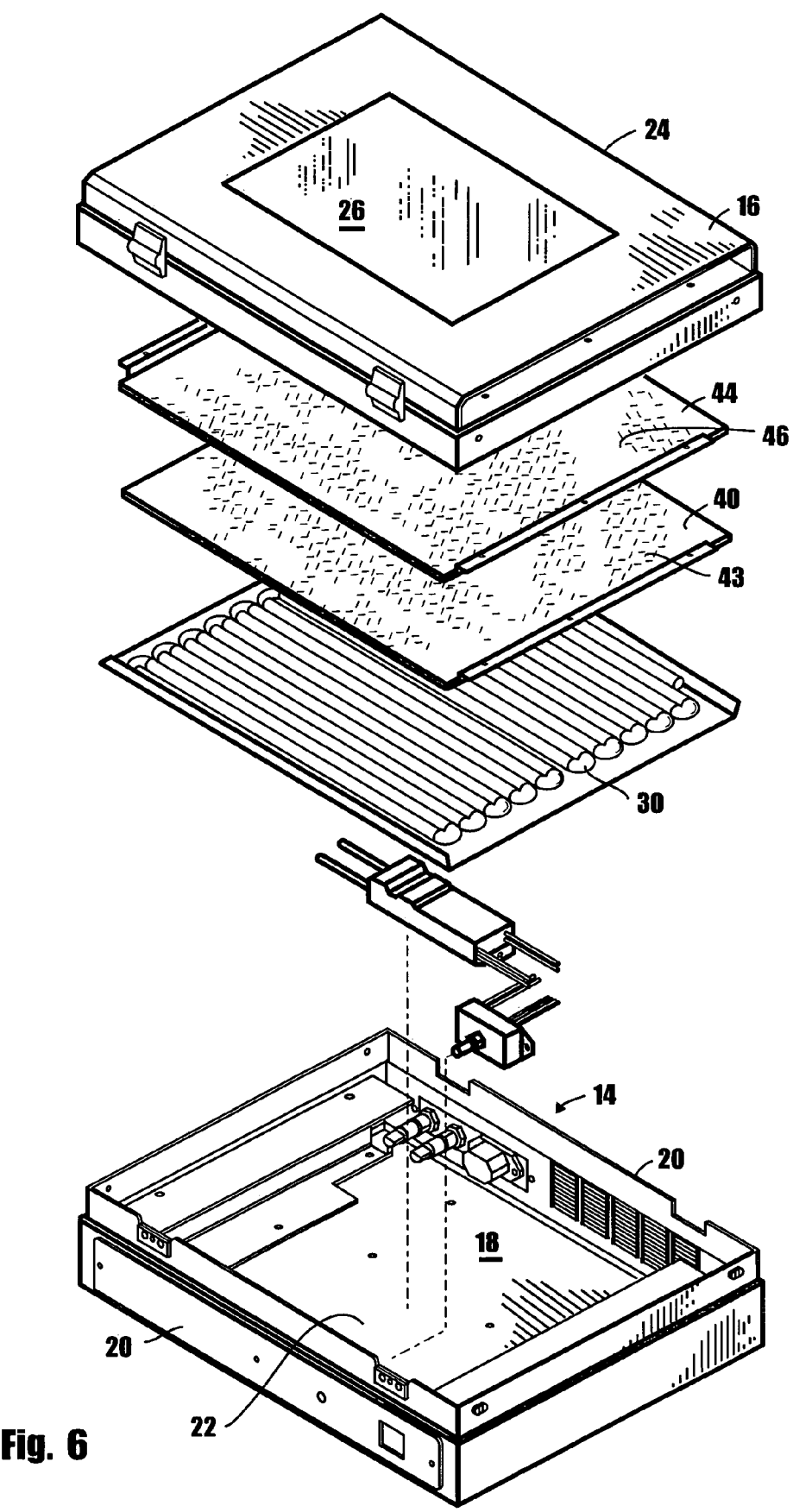
FIG. 6 is a generally perspective, exploded view of an alternate form of the apparatus of the invention for uniformly illuminating molecular samples with ultraviolet radiation.

Referring next to FIG. 6, still another form of transilluminator of the invention is there shown in generally diagrammatic form. This embodiment of the invention is also similar in many respects to that shown in FIG. 1 and like numerals are used in FIG. 6 to identify like components. This alternate form of the invention comprises a housing 14 having interconnected top, bottom and sidewalls, 16, 18 and 20 respectively that define an internal chamber 22. As before, top wall 16 includes a sample supporting area 26.

Positioned between the radiation means, or grid 30, are first and second wavelength conversion means which are adapted to convert the UV radiation at the first wavelength of, for example, 254 nanometers to UV radiation at a second wavelength of, for example, 302 nanometers and then to UV radiation at a third wavelength of, for example, 365 nanometers. This first wavelength conversion means here comprises a first conversion plate 40 that is carried by housing 14 at a location intermediate the sample support platform and the grid 30. In this instance, plate 40 is provided with a wave shifting phosphor coating 43. The second wavelength conversion means of this latest form of the invention comprises a second conversion plate 44 that is also carried by housing 14 at a location between conversion plate 40 and sample supporting platform 24. Plate 44 is provided with a wave shifting phosphor coating 46. It is to be understood that, with the construction shown in FIG. 6, either or both plates 40 and 44 can be removed from the housing and replaced with alternates plates if desired.

Figure 7:
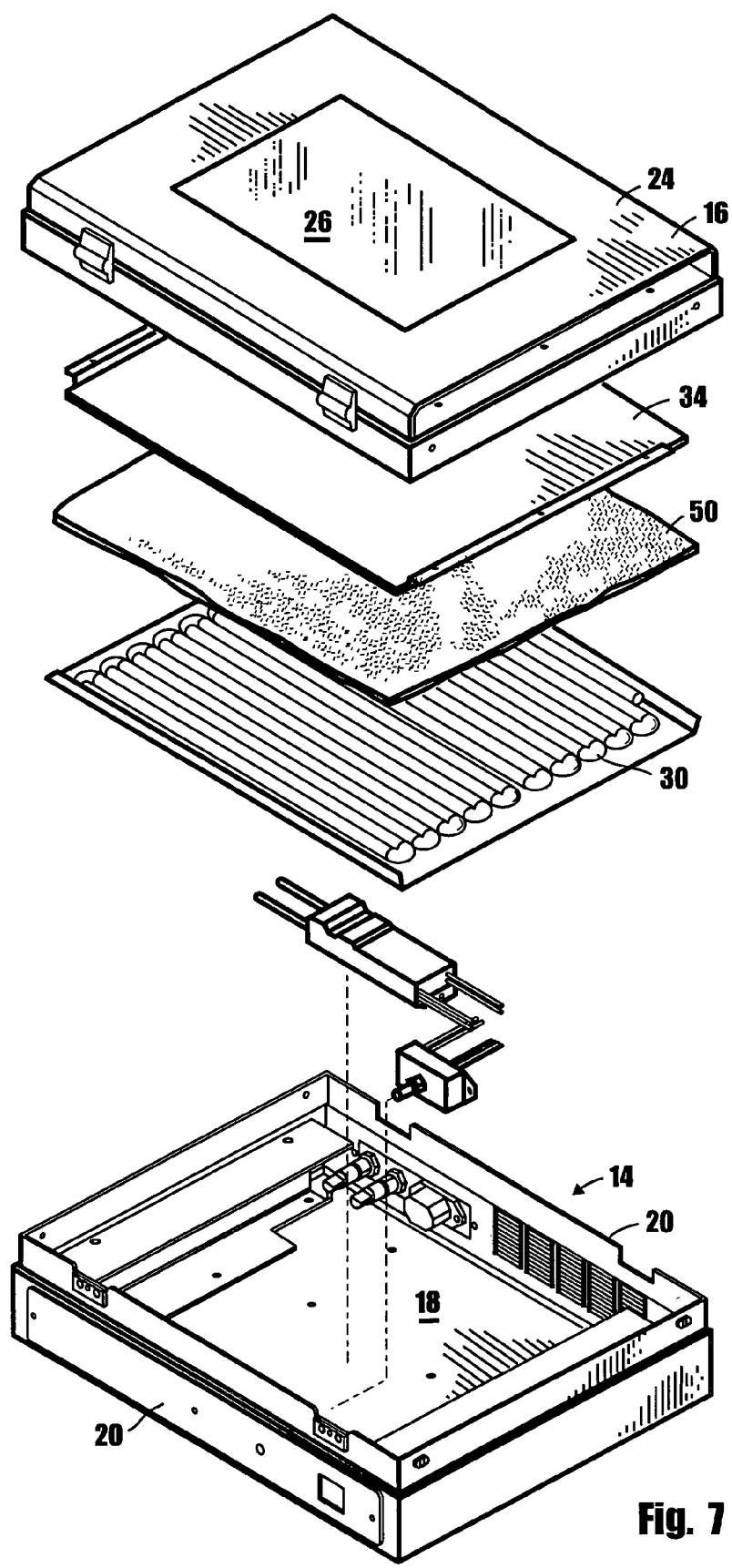
FIG. 7 is a generally perspective, exploded view of still another form of the apparatus of the invention for uniformly illuminating molecular samples with ultraviolet radiation.

Turning to FIG. 7, still another embodiment of the invention is there shown. This form of the invention is also similar in many respects to that shown in FIG. 1, and like numerals are once again used to identify like components. This alternate form of the invention comprises a housing 14 having interconnected top, bottom and sidewalls 16, 18 and 20. Carried by top wall 16 is a sample supporting platform 24 having a sample supporting area 26.

As illustrated in FIG. 7 of the drawings, the UV source once again comprises the uniquely configured grid 30 that emits UV radiation at a first wavelength of, for example, 254 nanometers. Positioned between grid 30 and the sample-supporting platform 24 is the novel previously mentioned dispersion means, here comprising a quartz fibrous mesh 50. This novel dispersion means, or fibrous mesh 50, functions to uniformly disperse the radiation generated by grid 30 in a manner to significantly contribute to the uniform illumination of the sample supporting platform 24. Disposed intermediate the dispersion means and the sample supporting platform 24 is a first wavelength conversion means, or conversion plate 34, that is carried within the internal chamber of housing 14 at a location intermediate the sample supporting platform and the fibrous mesh 50. More particularly, plate 34, which is of the character previously described, is adapted to convert the UV radiation at the first wavelength of about 254 nanometers to UV radiation at a second wavelength.

Turning once again to FIG. 2, this drawing comprises a graphical representation of the nonuniform illumination of the sample supporting platform which results from ultraviolet radiation emitted from a conventional transilluminator having six side-by-side, elongated tubular shaped lamp radiation sources (distances along the left and backside of the sample supporting platform are represented by the X and Y axes in FIG. 2, while radiation intensity is represented by the Z axis). The data shown in FIG. 2 was obtained using a bench top transilluminator manufactured and sold by UVP, Inc., of Upland, Calif. under the model designation M26X. This transilluminator uses six F8T5 302 nm 8-watt lamps and embodies a 25 cm×26 cm UV transmitting, ambient (visible light) blocking filter.

Figure 8:
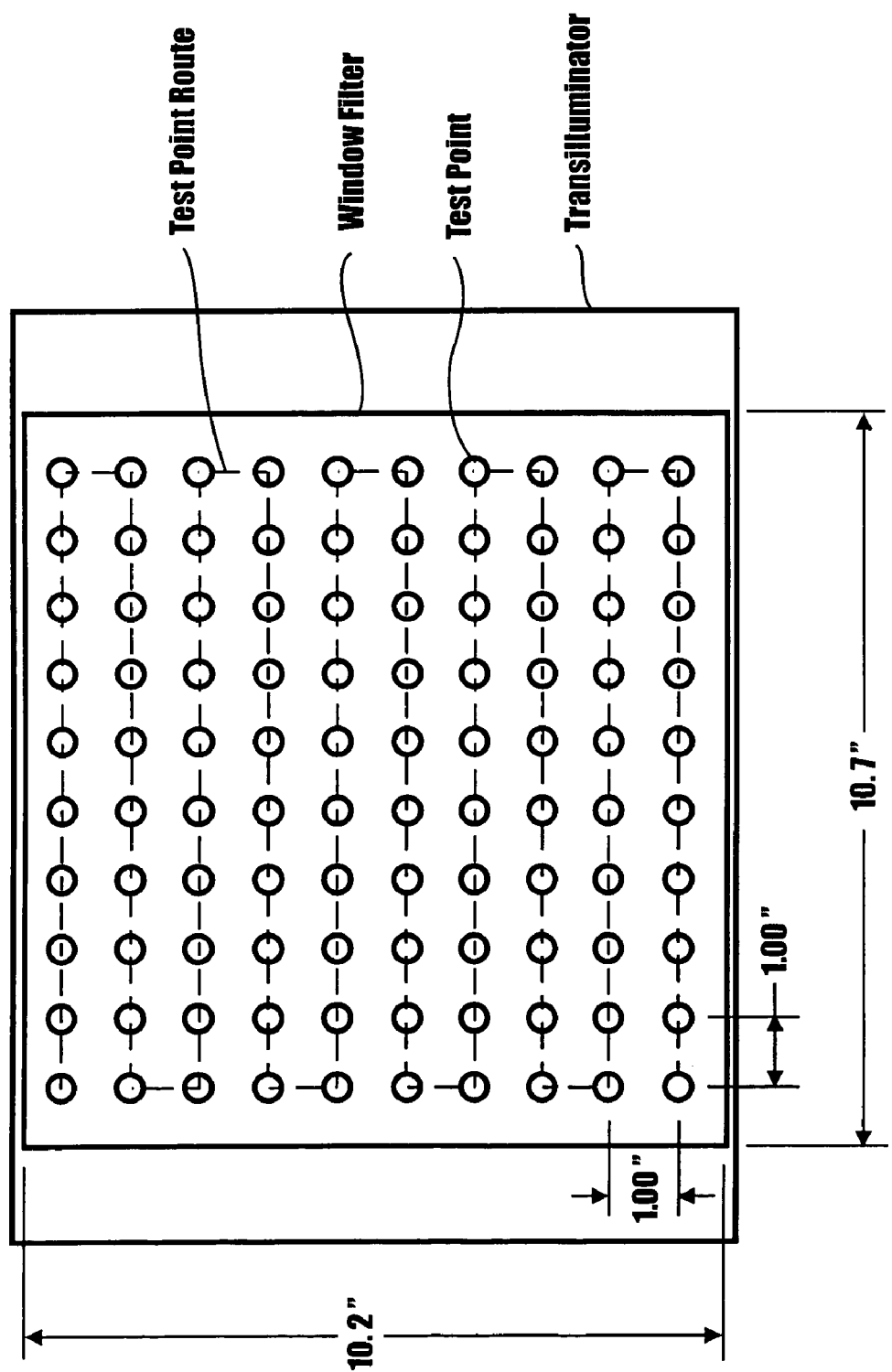
FIG. 8 is a generally diagrammatic view illustrating the manner in which the data shown in FIGS. 2 and 3 was obtained.

The data represented in FIG. 2 was obtained by measuring the intensity of the 302 nm radiation emitted by the ultraviolet lamps at 100 equally spaced (one inch apart) points 1.5 mm from the filter surface (see FIG. 8). The sensor used was a UVP, Inc. Model UVX-31 radiometer. The sensor was placed on each of the 100 points for 5 seconds and the intensity was recorded. The intensity of 185 nm radiation emitted by the lamps was measured in the center of the filter at a location 2 mm above the surface. The sensor used was a sensor that is commercially available from International Light of Newbury Port, Mass. under the model designation IL1700. In this instance the sensor was outfitted with a model SEE220 sensor head. This latter measurement was used to estimate the relative levels of ozone production.

As clearly shown in FIG. 2, the radiation intensity falls off markedly from the center of the sample supporting surface to the edges thereof. In the prior art of transilluminating the excitation light intensity is thus dependent on position of the sample on the sample-supporting platform, making quantitative side-by-side and sequential comparisons extremely difficult. Accordingly, the same sample will give very different fluorescent intensities depending on where the sample is placed on the sample-supporting platform of the typical prior art transilluminator.

FIG. 3 comprises a graphical representation of the substantially uniform illumination of the sample-supporting platform of the present invention, which results from ultraviolet radiation emitted from the uniquely configured radiation sources, or grid 30, of the apparatus. FIG. 3 clearly illustrates the dramatic improvement in the uniformity of excitation radiation across the sample supporting surface area 26 of the apparatus of the present invention when compared with the nonuniformity of radiation across the sample-supporting surface of the prior art transilluminator. With the coefficient of variation of (CV well below about 5 to 10% as illustrated in FIG. 3, meaningful, quantitative side-by-side comparisons are quite possible using the apparatus of the present invention. In addition, sequential analysis of several samples is also simplified and is substantially more accurate because of the minimal effect sample placement position has on excitation intensity. Stated another way, the sample will give substantially similar fluorescent intensities regardless of where the sample is positioned on the sample-supporting platform of the apparatus of the present invention.

In obtaining the data used to plot the graphical representations shown in FIGS. 2 and 3, the average intensity was calculated using the following formula:

$$\text{Output} = \frac{\sum_{i=1}^{n} X_i}{n}$$

The percent uniformity is the average of the row and column uniformity. This uniformity was calculated using the following formula:

Row uniformity=1-the tolerance of the row test point divided by the mean of the row test points (10)

Column uniformity=1-the tolerance of the column test point divided by the mean of the column test points (10)

Thus:

$$\text{Uniformity} = 1 - \frac{\max - \min}{\overline{X}},$$

$$\overline{X} = \frac{\sum_{i=1}^{n} X_i}{n}$$

The Coefficient of Variation (CV) is the standard deviation of the individual data points divided by the average. More specifically, the CV is a relative measure of variation and independent of units, and is ideal for evaluating results from different experiments that use the same basic test or instrument. In this case, variations of the transillumination intensity across various transilluminator designs were quantified and compared. The lower the CV, the smaller the variation of intensity across the active area of the transilluminator.

$$\text{Coefficient of Variation} = \frac{s}{\overline{X}}$$

$$s = \sqrt{\frac{\sum_{i=1}^{n} (X_i - \overline{X})^2}{n-1}}$$

$$\overline{X} = \frac{\sum_{i=1}^{n} \overline{X}_i}{n}$$

It is to be noted that the Coefficient of Variation times 100=percentage.

A study of FIGS. 2 and 3 clearly demonstrates the value of the present invention and the substantial advancement over the prior art that it represents.

Having now described the invention in detail in accordance with the requirements of the patent statutes, those skilled in this art will have no difficulty in making changes and modifications in the individual parts or their relative assembly in order to meet specific requirements or conditions. Such changes and modifications may be made without departing from the scope and spirit of the invention, as set forth in the following claims.

I claim:

1. An apparatus for uniformly illuminating molecular samples with ultraviolet radiation comprising:
    (a) a housing including an internal chamber and a sample supporting platform having a sample supporting area;
    (b) radiation means disposed within said chamber for uniformly irradiating said sample supporting area with ultraviolet light at a first wavelength, said radiation means comprising a grid for emitting ultraviolet radiation constructed from a serpentine shaped ultraviolet light producing tube; and
    (c) a first conversion means removably carried by said housing at a location intermediate said radiation means and said sample supporting platform for converting the radiation emitted from said source of ultraviolet radiation to radiation at a second wavelength.

2. The apparatus as defined in claim 1 in which said serpentine shaped ultraviolet tube comprises a continuous tube that is strategically formed to provide a multiplicity of side-by-side, immediately adjacent irradiating segments.

3. The apparatus as defined in claim 1 in which said radiation means further comprises dispersion means superimposed over said grid for controllably disbursing the ultraviolet radiation emitted from said grid.

4. The apparatus as defined in claim 1 in which said radiation means source of ultraviolet radiation emits radiation at a wave length of about 254 nanometers and in which said first conversion means converts the radiation to approximately 365 nanometers.

5. An apparatus as defined in claim 1 in which said source of ultraviolet radiation emits radiation at a wave length of about 254 nanometers and in which said first conversion means converts the radiation to approximately 300 nanometers.

6. An apparatus as defined in claim 1 in which said first conversion means comprises a conversion plate having a phosphor coating.

7. An apparatus as defined in claim 1 further including a second conversion means removably carried by said housing at a location intermediate said first conversion means and said sample supporting platform for converting the radiation emitted for said radiation means to radiation at a third wavelength.

8. An apparatus as defined in claim 7 in which said radiation means emits radiation at a wave length of about 254 nanometers, in which said first conversion means converts the radiation to approximately 300 nanometers and in which said second conversion means converts the radiation to approximately 365 nanometers.

9. An apparatus for uniformly illuminating molecular samples with ultraviolet radiation comprising:
    (a) a housing having interconnected top, bottom, and side walls defining an internal chamber and a sample supporting platform having a sample supporting area;
    (b) radiation means disposed within said chamber for uniformly irradiating said sample supporting area with ultraviolet light at a first wavelength, said radiation means comprising a grid for emitting ultraviolet radiation constructed from a continuous, serpentine shaped ultraviolet tube that is strategically formed to provide a multiplicity of side-by-side, immediately adjacent irradiating segments; and
    (c) a first conversion means removably carried by said housing at a location intermediate said radiation means and said sample supporting platform for converting the radiation emitted from said source of ultraviolet radiation to radiation at a second wavelength.

10. The apparatus as defined in claim 9 in which said radiation means further comprises dispersion means superimposed over said grid for controllably discussing the ultraviolet radiation emitted from said grid, said dispersion means comprising a quartz fibrous mesh.

11. The apparatus as defined in claim 9 in which said radiation means source of ultraviolet radiation emits radiation at a wave length of about 254 nanometers and in which said first conversion means converts the radiation to approximately 365 nanometers.

12. The apparatus as defined in claim 9 in which said source of ultraviolet radiation emits radiation at a wave length of about 254 nanometers and in which said first conversion means converts the radiation to approximately 300 nanometers.

13. The apparatus as defined in claim 9 in which said first conversion means comprises a conversion plate having a phosphor coating.

14. The apparatus as defined in claim 9 in which a plurality of segments are coated with phosphor.

15. The apparatus as defined in claim 9 further including a reflector disposed within said housing between said bottom wall and said radiation means.

16. The apparatus as defined in claim 9 further including a phosphor coated borosilicate plate disposed between said bottom wall and said radiation means.

17. The apparatus as defined in claim 9 further including a second conversion means carried by said housing at a location intermediate said first conversion means and said sample supporting platform for converting the radiation emitted from said radiation means to radiation at a third wavelength.

18. The apparatus as defined in claim 17 in which said radiation means emits radiation at a wave length of about 254 nanometers, in which said first conversion means converts the radiation to approximately 300 nanometers and in which said second conversion means converts the radiation to approximately 365 nanometers.

19. A method of uniformly illuminating molecular samples with ultraviolet radiation using an apparatus comprising a housing having a floor, an internal chamber and a sample supporting platform; radiation means disposed within the chamber for directing radiation at a first wavelength in a direction toward the floor and toward the sample supporting platform; first conversion means carried by the housing at a location intermediate the radiation means and the sample supporting platform for converting the radiation emitted from the source of radiation to radiation at a second wavelength; second conversion means carried by the floor for converting the radiation emitted from the source of ultraviolet radiation to radiation at a second wavelength and a reflector disposed within the housing at a location below the radiation means and above the floor; the method comprising the steps of:

(a) using the first conversion means, converting the radiation directed toward the sample supporting platform to a first converted radiation wavelength;

(b) using the second conversion means, converting the radiation directed toward the floor to a second converted radiation wavelength;

(c) using the reflector, reflecting said second converted radiation in a direction toward the first conversion means;

(d) adding said first converted radiation to said second converted radiation to produce a sample irradiating radiation; and (e) irradiating the samples with said sample irradiating radiation.

20. The method as defined in claim 19 in which the first wavelength is approximately 254 nm and in which said first converted radiation is approximately 302 nm.

21. The method as defined in claim 19 in which the first wavelength is approximately 254 nm and in which said second converted radiation is approximately 365 nm.

* * * * *